United States Patent [19]
Sorenson

[11] Patent Number: 6,020,124
[45] Date of Patent: *Feb. 1, 2000

[54] DETECTION OF SOLUBLE GENE SEQUENCES IN BIOLOGICAL FLUIDS

[75] Inventor: George D. Sorenson, Meriden, N.H.

[73] Assignee: Trustees of Dartmouth College, Hanover, N.H.

[*] Notice: This patent is subject to a terminal disclaimer.

[21] Appl. No.: 08/483,746

[22] Filed: Jun. 7, 1995

Related U.S. Application Data

[63] Continuation-in-part of application No. 08/142,845, Oct. 25, 1993, Pat. No. 5,496,699, which is a continuation of application No. 07/874,845, Apr. 27, 1992, abandoned.

[51] Int. Cl.[7] ................................................ C12Q 1/68
[52] U.S. Cl. .............................. 435/6; 536/24.3; 435/91.2
[58] Field of Search .................... 435/6, 91.2; 536/24.31, 536/24.3, 24.33

[56] References Cited

U.S. PATENT DOCUMENTS

| | | | |
|---|---|---|---|
| 4,988,617 | 1/1991 | Landgren et al. | 435/6 |
| 5,068,175 | 11/1991 | Prashad | 435/6 |
| 5,137,806 | 8/1992 | LeMaistre et al. | 435/6 |

FOREIGN PATENT DOCUMENTS

| | | |
|---|---|---|
| WO 87/02064 | 4/1987 | WIPO . |
| WO 89/00206 | 1/1989 | WIPO . |
| WO 93/22456 | 11/1993 | WIPO . |
| WO 93/25706 | 12/1993 | WIPO . |
| WO 95/14790 | 6/1995 | WIPO . |
| WO 96/13611 | 5/1996 | WIPO . |

OTHER PUBLICATIONS

Almarsson et al., Proc. Natl. Acad. Sci., 90:7518–7522, Aug. 1993.

Barany, F. (1991) "Genetic disease detection and DNA amplification using cloned thermostable ligase" *PNAS USA* 88:189–193.

Barany, F. (1991) "The Ligase Chain Reaction in a PCR World" *PCR Methods and Applications* 1:5–16.

Dennin, R.H. (1979) "DNA of Free and Complexed Origin in Human Plasma: Concentration and Length Distribution" *Klin. Wochenschr.* 57:451–456.

Fournié, G.J. et al. (1986) "Recovery of Nanogram Quantities of DNA from Plasma and Quatitative Measurement Using Labeling by Nick Translation" *Analy. Biochem.* 158:250–256.

Gilliland, G. et al. (1990) "Analysis of cytokine mRNA and DNA: Detection and quantitation by competitive polymerase chain reaction" *PNAS USA* 87:2725–2729.

Gilliand, G. et al. (1990) "Competitive PCR for Quantitation of mRNA" in *PCR Protocols: A Guide to Methods and Applications*, M.A. Innis et al., Eds. (San Diego, CA: Academic Press Inc.) Chp. 8:60–69.

Higuchi, R. et al. (1988) "A general method of in vitro preparation and specific mutagenesis of DNA fragments: study of protein and DNA interactions" *Nucleic Acids Research* 16(15):7351–7367.

Kwok, S. et al. (1990) "Effects of primer–template mismatches on the polymerase chain reaction: Human immunodeficiency virus type 1 model studies" *Nucleic Acids Research* 18(4):999–1005.

(List continued on next page.)

*Primary Examiner*—George C. Elliott
*Assistant Examiner*—Scott W. Houtteman
*Attorney, Agent, or Firm*—Jean M. Silveri; Lahive & Cockfield, LLP

[57] ABSTRACT

Methods are provided for detecting and quantitating gene sequences, such as mutated genes and oncogenes, in biological fluids. The fluid sample (e.g., plasma, serum, urine, etc.) is obtained, deproteinized and the DNA present in the sample is extracted. The DNA is then amplified using an amplification procedure, such as PCR or LCR, to amplify the mutated gene sequence. In one embodiment, the DNA is contacted with a peptide nucleic acid prior to or during the amplification procedure.

24 Claims, 8 Drawing Sheets

OTHER PUBLICATIONS

Landgraf, A. et al. (1991) "Quantitative Analysis of Polymerase Chain Reaction (PCR) Products Using Primers Labeled with Biotin and a Fluorescent Dye" *Analy. Biochem. 193*:231–235.

Lawyer, F.C. et al. (1993) "High–level Expression, Purification, and Enzymatic Characterization of Full–length *Thermus aquaticus* DNA Polymerase and a Truncated Form Deficient in 5' to 3' Exonuclease Activity" *PCR Methods and Applications 2*:275–287.

Leon, S.A. et al. (1977) "Free DNA in the Serum of Cancer Patients and the Effect of Therapy" *Cancer Research 37*:646–650.

Martin, M. et al. (1992) "A Method for Using Serum or Plasma as a Source of DNA for HLA Typing" *Human Immunology 33*:108–113.

Murakami, Y. et al. (1991) "Detection of Aberrations of the p53 Alleles and the Gene Transcript in Human Tumor Cell Lines by Single–Strand Conformation Polymorphism Analysis" *Cancer Research 51*:3356–3361.

Nickerson, D.A. et al. (1990) "Automated DNA diagnostics using an ELISA–based oligonucleotide ligation assay" *PNAS USA 87*:8923–8927.

Nielson, P.E. et al. (1993) "Sequence specific inhibition of DNA restriction enzyme cleavage by PNA" *Nucleic Acids 21*(2):197–200.

Ørum, H. et al. (1993) "Single base pair mutation analysis by PNA directed PCR clamping" *Nucleic Acids Research 21*(23):5332–5336.

Saiki, R.K. (1990) "Amplification of Genomic DNA" in *PCR Protocols: A Guide to Methods and Applications*, M.A. Innis et al., Eds. (San Diego, CA: Academic Press Inc.) Chp.2:13–20.

Shapiro, B. et al. (1983) "Determination of Circulating DNA Levels in Patients with Benign or Malignant Gastrointestinal Disease" *Cancer 51*:2116–2120.

Sidransky, D. et al. (1992) "Identification of ras Oncogene Mutations in the Stool of Patients with Curable Colorectal Tumors" *Science 256*:102–105.

Steinman, C.R. (1984) "Circulating DNA in Systemic Lupus Erythematosus: Isolation and Characterization" *J. Clin. Invest. 73*:832–841.

Stork, P. et al. (1991) "Detection of K–ras mutations in pancreatic and hepatic neoplasms by non–isotopic mismatched polymerase chain reaction" *Oncogene 6*:857–862.

Stratgene (1988) "Table of Contents" in *Stratagene Catalog: Gene Characterization Kits*, 39.

Vallette F. et al. (1989) "Construction of mutant and chimeric genes using the polymerase chain reaction" *Nucleic Acids Research 17*(2):723–733.

Verlaan–de Vries, M. et al. (1986) "A dot–blot screening procedure for mutated ras oncogenes using synthetic oligodeoxynucleotides" *Gene 50*:313–320.

Weiss, R. (1991) "Hot Prospect for New Gene Amplifier" *Science 254*:1292–1293.

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

GCCTACGCCA CCAGCTCCAA                                    20

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

GTGGTAGTTG GAGCTG                                                          16

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GTGGTAGTT GGAGCTC                                                          16

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GTGGTAGTTG GAGCTT                                                          16

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GTGGTAGTTG GAGCTA                                                          16

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CAGAGAAACC TTTATCTG                                                        18

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ACTCTTGCCT ACGCCAC                                                         17

-continued (2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ACTCTTGCCT ACGCCAG                                    17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

ACTCTTGCCT ACGCCAT                                    17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

ACTCTTGCCT ACGCCAA                                    17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GTACTGGTGG AGTATTT                                    17

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

AGCTCCAACT ACCACAAGTT                                   20

(2) INFORMATION FOR SEQ ID NO:13:

(i) SEQUENCE CHARACTERISTICS:
        (A) LENGTH: 20 base pairs

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GCACTCTTGC CTACGCCACC                                                        20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCACTCTTGC CTACGCCACA                                                        20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GCACTCTTGC CTACGCCACG                                                        20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCACTCTTGC CTACGCCACT                                                        20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GGTGGCGTAG GCAAGAGTGC                                                        20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:18:

AACTTGTGGT AGTTGGAGCT                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

AACTTGTGGT AGTTGGAGCA                    20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

AACTTGTGGT AGTTGGAGCC                    20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

AACTTGTGGT AGTTGGAGCG                    20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GCCTGCTGAA AATGACTGAA                    20

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CATCCGTTCT CACGGAACTG CTATGTCGAT         30

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

TATGTCGATT AAGTCTTAGT                                        20

DETECTION OF SOLUBLE GENE SEQUENCES IN BIOLOGICAL FLUIDS

RELATED APPLICATIONS

This application is a continuation-in-part application of U.S. patent application Ser. No. 08/142,845, filed Oct. 25, 1993, now U.S. Pat. No. 5,496,699, which is a continuation application of U.S. patent application Ser. No. 07/874,845, filed Apr. 27, 1992 now abandoned. The contents of these prior applications are hereby incorporated by reference.

GOVERNMENT SUPPORT

The research leading to this invention was supported by government funding pursuant to NIH Grant Nos. CA 47248 and CA 58625.

BACKGROUND OF THE INVENTION

Soluble DNA is known to exist in the blood of healthy individuals at concentrations of about 5 to 10 ng/ml. It is believed that soluble DNA is present in increased levels in the blood of individuals having autoimmune diseases, particularly systemic lupus erythematosus (SLE) and other diseases including viral hepatitis, cancer and pulmonary embolism. It is not known whether circulating soluble DNA represents a specific type of DNA which is particularly prone to appear in the blood. However, studies indicate that the DNA behaves as double-stranded DNA or as a mixture of double-stranded and single-stranded DNA, and that it is likely to be composed of native DNA with single-stranded regions. Dennin, R. H. (1979) *Klin. Wochenschr.* 57:451–456. Steinman, C. R. (1984) *J. Clin. Invest.* 73:832–841. Fournie, G. J. et al. (1986) *Analytical Biochem.* 158:250–256. There is also evidence that in patients with SLE, the circulating DNA is enriched for human repetitive sequence (Alu) containing fragments when compared to normal human genomic DNA.

In patients with cancer, the levels of circulating soluble DNA in blood are significantly increased. Types of cancers which appear to have a high incidence of elevated DNA levels include pancreatic carcinoma, breast carcinoma, colorectal carcinoma and pulmonary carcinoma. In these forms of cancer, the levels of circulating soluble DNA in blood are usually over 50 ng/ml, and generally the mean values are more than 150 ng/ml. Leon et al. (1977) *Can. Res.* 37:646–650; Shapiro et al. (1983) *Cancer* 51:2116–2120.

Mutated oncogenes have been described in experimental and human tumors. In some instances certain mutated oncogenes are associated with particular types of tumors. Examples of these are adenocarcinomas of the pancreas, colon and lung which have approximately a 75%, 50%, and 35% incidence respectively, of Kirsten ras (K-ras) genes with mutations in positions 1 or 2 of codons 12. The most frequent mutations are changes from glycine to valine (GGT to GTT), glycine to cysteine (GGT to TGT), and glycine to aspartic acid (GGT to GAT). Other, but less common mutations of codon 12 include mutations to AGT and CGT. K-ras genes in somatic cells of such patients are not mutated.

The ability to detect sequences of mutated oncogenes or other genes in small samples of biological fluid, such as blood plasma, would provide a useful diagnostic tool. The presence of mutated K-ras gene sequences in the plasma would be indicative of the presence in the patient of a tumor which contains mutated oncogenes. Presumably this would be a specific tumor marker since there is no other known source of mutated K-ras genes. Therefore, this evaluation may be useful in suggesting and/or confirming a diagnosis. The amount of mutated K-ras sequences in the plasma may relate to the size of the tumor, the growth rate of the tumor and/or the regression of the tumor. Therefore, serial quantitation of mutated K-ras sequences may be useful in determining changes in tumor mass. Since most human cancers have mutated oncogenes, evaluation of plasma DNA for mutated sequences may have very wide applicability and usefulness.

SUMMARY OF THE INVENTION

This invention recognizes that gene sequences (e.g., oncogene sequences) exist in blood, and provides a method for detecting and quantitating gene sequences such as from mutated oncogenes and other genes in biological fluids, such as blood plasma and serum. The method can be used as a diagnostic technique to detect certain cancers and other diseases which tend to increase levels of circulating soluble DNA in blood. Moreover, this method is useful in assessing the progress of treatment regimes for patients with certain cancers.

The method of the invention involves the initial steps of obtaining a sample of biological fluid (e.g., urine, blood plasma or serum, sputum, colonic effluent, fluid from endoscopic retrograde cholangeopancreatography, cerebrospinal fluid, bone marrow, or lymph), then deproteinizing and extracting the DNA. After extraction of the DNA, mutant alleles therein can be detected using embodiments of the method of the present invention.

In one embodiment, the extracted DNA is amplified by techniques such as the polymerase chain reaction (PCR) or the ligase chain reaction (LCR) in an allele-specific manner to distinguish a normal gene sequence from a mutated gene sequence present in the sample. This amplification step can be preceded by a common amplification step in which the wild-type and/or the mutated DNA is amplified to increase the total amount of DNA from which the mutant allele can be detected.

In another embodiment, the extracted DNA is contacted with a peptide nucleic acid (PNA) which is complementary to a segment of the DNA, e.g., a segment of the wild-type sense strand. The peptide nucleic acid binds to the DNA (termed "strand displacement" herein) and thereby interferes with subsequent amplification of the sequence, e.g., wild-type sequence. In addition, a PNA can be contacted (i.e., incubated) with the DNA at any one step or at more than one step of the method described herein. For example, the PNA can be incubated with the DNA after the DNA is first extracted and/or during amplification, e.g., common amplification or allele-specific amplification of the DNA. Moreover, steps from any of the embodiments of the present method can be combined into one method. The effect of the above-described uses of PNAs is a substantial decrease in the number of false positives derived from mismatching and extension from wild-type DNA sequences.

Where the location of the mutation is known, the allele-specific PCR amplification is performed using four pairs of oligonucleotide primers. The four primer pairs include a set of four allele-specific first primers complementary to the gene sequence contiguous with the site of the mutation on the first strand. These four primers are unique with respect to each other and differ only at the 3' nucleotide which is complementary to the wild type nucleotide or to one of the three possible mutations which can occur at this known position. The four primer pairs also include a single common primer which is used in combination with each of the four unique first strand primers. The common primer is complementary to a segment of a second strand of the DNA, at some distance from the position of the first primer.

This amplification procedure amplifies a known base pair fragment which includes the mutation. Accordingly, this technique has the advantage of displaying a high level of sensitivity since it is able to detect only a few mutated DNA sequences in a background of a $10^5$-fold excess of normal DNA. The method is believed to be of much greater sensitivity than methods which detect point mutations by hybridization of a PCR product with allele-specific radiolabelled probes which will not detect a mutation if the normal DNA is in more than 20-fold excess.

The above embodiment is useful where a mutation exists at a known location on the DNA. In another embodiment where the mutation is known to exist in one of two possible positions, eight pair of oligonucleotide primers may be used. The first set of four primer pairs (i.e., the four unique, allele-specific primers, each of which forms a pair with a common primer) is as described above. The second set of four primer pairs comprises four allele-specific primers complementary to the gene sequence contiguous with the site of the second possible mutation on the sense strand. These four primers are unique with respect to each other and differ at the terminal 3' nucleotide which is complementary to the wild type nucleotide or to one of the three possible mutations which can occur at this second known position. Each of these allele-specific primers is paired with another common primer complementary to the other strand, distant from the location of the mutation.

The PCR techniques described above preferably utilize a DNA polymerase which lacks 3' exonuclease activity and therefore the ability to proofread. A preferred DNA polymerase is *Thermus aquaticus* DNA polymerase.

During the amplification procedure, it is usually sufficient to conduct approximately 30 cycles of amplification in a DNA thermal cycler. After an initial denaturation period of 5 minutes, each amplification cycle includes a denaturation period of about 1 minute at 95° C., primer annealing for about 2 minutes at 58° C. and an extension at 72° C. for approximately 1 minute.

In a preferred embodiment, approximately 30 cycles of amplification in a DNA thermal cycler are conducted. After an initial denaturation period of 5 minutes at 94° C., each amplification cycle includes an additional denaturation period of about 1 minute at 94° C., PNA annealing for a period of about thirty seconds at 75° C., primer annealing for a period of about 1 minute at 65° C., and an extension for a period of about 1 minute at 70° C.

Following the amplification, aliquots of amplified DNA from the PCR can be analyzed by techniques such as electrophoresis through agarose gel using ethidium bromide staining. Improved sensitivity may be attained by using labelled primers and subsequently identifying the amplified product by detecting radioactivity or chemiluminescense on film. Labelled primers may also permit quantitation of the amplified product which may be used to determine the amount of target sequence in the original specimen.

As used herein, allele-specific amplification describes a feature of the method of the invention where primers are used which are specific to a mutant allele, thus enabling amplification of the sequence to occur where there is 100% complementarity between the 3' end of the primer and the target gene sequence. Thus, allele-specific amplification is advantageous in that it does not permit amplification unless there is a mutated allele. This provides an extremely sensitive detection technique.

DETAILED DESCRIPTION OF THE INVENTION

Figure 1A:
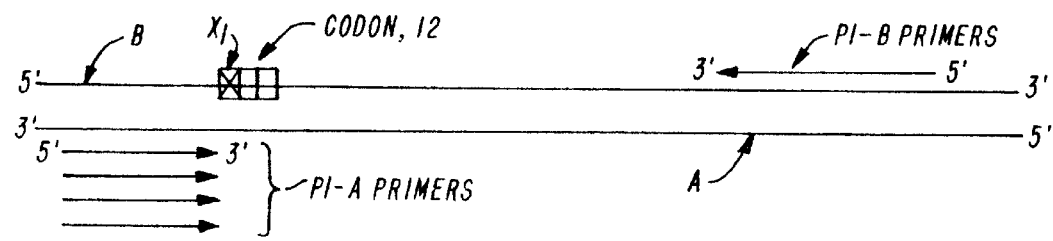
FIGS. 1A–1B are diagramatic representations of the amplification strategy for the detection of a mutated K-ras gene with a mutation present at a single known location of K-ras.

The detection of mutated DNA, such as specific single copy genes, is useful for diagnostic purposes, and/or for evaluating the extent of a disease. Normal plasma is believed to contain about 10 ng of soluble DNA per ml. The concentration of soluble DNA in blood plasma is known to increase markedly in individuals with cancer and some other diseases. The ability to detect the presence of known mutated gene sequences, such as K-ras gene sequences, which are indicative of a medical condition, is thus highly desirable.

The present invention provides a highly sensitive diagnostic method enabling the detection of such mutant alleles in biological fluid, even against a background of as much as a $10^5$-fold excess of normal DNA. The method generally involves the steps of obtaining a sample of a biological fluid containing soluble DNA, deproteinizing, extracting and denaturing the DNA, followed by amplifying the DNA in an allele-specific manner, using a set of primers among which is a primer specific for the mutated allele. Through this allele-specific amplification technique, only the mutant allele is amplified. Following amplification, various techniques can be employed to detect the presence of amplified DNA and to quantify the amplified DNA. The presence of the amplified DNA represents the presence of the mutated gene, and the amount of the amplified gene present can provide an indication of the extent of a disease.

This technique is applicable to the identification in biological fluid of sequences from single copy genes, mutated at a known position on the gene. Samples of biological fluid having soluble DNA (e.g., blood plasma, serum, urine, sputum, colonic effluent, fluid from endoscopic retrograde cholangeopancreatography, cerebrospinal fluid, bone marrow, and lymph) are collected and treated to deproteinize and extract the DNA. Thereafter, the gene bearing the mutation is amplified in an allele-specific manner using an embodiment of the method of the present invention.

During deproteinization of DNA from the fluid sample, the rapid removal of protein and the virtual simultaneous deactivation of any DNase is believed to be important. In one embodiment of the invention, DNA is deproteinized by adding to aliquots of the sample an equal volume of 20% NaCl and then boiling the mixture for about 3 to 4 minutes. Subsequently, standard techniques can be used to complete the extraction and isolation of the DNA. A preferred extraction process involves concentrating the amount of DNA in the fluid sample by techniques such as centrifugation.

In a preferred embodiment of the invention, the DNA is isolated from the sample of biological fluid using the method described in Example IV using, for example, Qiagen's QIAamp Blood kit.

The use of the 20% NaCl solution, followed by boiling, is believed to rapidly remove protein and simultaneously inactivate any DNases present. DNA present in the plasma is believed to be in the form of nucleosomes and is thus believed to be protected from the DNases while in blood. However, once the DNA is extracted, it is susceptible to the DNases. Thus, it is important to inactivate the DNases at the same time as deproteinization to prevent the DNases from inhibiting the amplification process by reducing the amount of DNA available for amplification. Although the 20% NaCl solution is currently preferred, it is understood that other concentrations of NaCl, and other salts, can also be used.

Other techniques may also be used to extract the DNA while preventing the DNases from affecting the available DNA. Because plasma DNA is believed to be in the form of nucleosomes (mainly histones and DNA), plasma DNA could also be isolated using an antibody to histones or other nucleosomal proteins. Another approach could be to pass the plasma (or serum) over a solid support with attached antihistone antibodies which would bind with the nucleosomes. After rinsing the nucleosomes can be eluted from the antibodies as an enriched or purified fraction. Subsequently, DNA can be extracted using the above or other conventional methods. In one embodiment of the present invention, the extracted DNA can then be denatured and amplified in an allele-specific manner.

In another and preferred embodiment of the invention the DNA, once extracted, is contacted with (i.e., incubated with) a peptide nucleic acid (PNA) designed to be complementary to a segment of either strand of wild-type DNA. Preferably, the PNA is designed to be complementary to a segment on the sense strand of the wild-type DNA at which a spanning primer in the common amplification step binds. For example, the PNA can be complementary to a segment on the sense strand of wild-type DNA which overlaps with a segment on the sense strand with which a spanning primer is complementary. Once contacted with the DNA, the PNA invades the double-stranded DNA structure and binds to its complementary DNA segment to form a D-loop of single-stranded DNA. See e.g., PerSeptive Biosystems 1994 Bioresearch Products Brochure. The PNA bound to the wild-type DNA blocks access of the amplification primers to the wild-type DNA. The overall result of this blockage is a significant decrease in false positives produced by the method of the invention. The use of PNA in the method of the present invention can allow for detection of mutant alleles in the presence of about $10^5$ excess of wild-type DNA. To eliminate the possibility that the single DNA strand forming the D-loop will be amplified, the PNA/DNA complex can be treated with a nuclease, e.g., S1 nuclease, micrococcal nuclease, to cut the D-loop. The PNA can be incubated with the extracted DNA prior to the common amplification step, during the common amplification step, and/or during the allele-specific amplification step.

PNA oligomers are commercially available from, for example, PerSeptive Biosystems, and can be custom synthesized to certain specifications. Preferably, the PNAs used in the method of the present invention are at least about 10, more preferably at least about 15, yet more preferably at least about 20 nucleotides in length. The PNAs used in the present method are typically synthesized such that they are complementary to a segment or portion of a strand, e.g., the sense or antisense strand, of wild-type DNA. In addition, several PNAs can be synthesized each of which is complementary to a segment or portion of a different strand of the wild-type DNA, e.g., one PNA can be complementary to a segment of the sense strand of the DNA and the other PNA can be complementary to the antisense strand of the DNA. Preferably, the PNAs are synthesized such that they are complementary to a segment of the wild-type DNA which overlaps with the segment of the DNA to which the spanning primers in the common amplification step bind. Binding or "clamping" of the PNAs to the wild-type DNA inhibits or interferes with amplification of wild-type sequences and significantly decreases the possibility of low incidence mismatch priming and extension which otherwise leads to false positive reactions in the presence of relatively high concentrations of wild-type DNA. An illustrative example of a PNA nucleotide sequence of a PNA which can be used in the present invention is H-GCC-TAC-GCC-ACC-AGC-TCC-AA-NH$_2$ (SEQ ID NO:1)

Peptide nucleic acids are analogs of DNA in which the phosphate backbone is replaced with a peptide-like backbone. The purine (A, G) and pyrimidine (C, T) bases are attached to the backbone by methylene carbonyl linkages. Some properties of the PNAs which allow them to bind wild-type sequence stably and effectively include: (1) a higher thermal stability of complementary PNA/DNA duplexes than that of corresponding DNA/DNA duplexes. For example, for a PNA/DNA duplex fifteen nucleotides in length, the increase in $T_m$ over a DNA/DNA duplex is about 15° C.; (2) a greater specificity of interaction of PNA/DNA hybrids which means that a single nucleotide mismatch in PNA/DNA duplexes is more destabilizing than a corresponding mismatch in DNA/DNA duplexes. For example, a single mismatch in a PNA/DNA fifteen nucleotides in length lowers the $T_m$ about 15° C. while a corresponding mismatch in DNA/DNA lowers the $T_m$ about 11° C.; and (3) the unrecognizability of PNAs to DNA polymerases which fail to extend PNAs. Use of PNAs in the method of the present invention is also advantageous in that the polyamide backbone with purine and pyrimidine base side chains of PNAs is not easily recognizable by either nucleases or proteases and in that PNAs are stable over a wide pH range.

In one embodiment, the allele-specific amplification is performed through the Polymerase Chain Reaction (PCR) using primers having 3' terminal nucleotides complementary to specific point mutations of a gene for which detection is sought. PCR preferably is conducted by the method described by Saiki, "Amplification of Genomic DNA", *PCR Protocols,* Eds. M. A. Innis, et al., Academic Press, San Diego (1990), pp. 13. In addition, the PCR is conducted using a thermostable DNA polymerase which lacks 3' exonuclease activity and therefore the ability to repair single base mismatches at the 3' terminal nucleotide of the DNA primer during amplification. As noted, a preferred DNA polymerase is *T. aquaticus* DNA polymerase. A suitable *T. aquaticus* DNA polymerases is commercially available from Perkin-Elmer as AmpliTaq DNA polymerase. Another preferred polymerase is the AmpliTaq Stoffel fragment DNA polymerase which is deficient in 5' to 3' exonuclease activity. See Lawyer, F. C. et al. (1993) *PCR Methods and Applications* 2:275–287. Other useful DNA polymerases which lack 3' exonuclease activity include a Vent$_R$ (exo-), available from New England Biolabs, Inc., (purified from strains of *E. coli* that carry a DNA polymerase gene from the archaebacterium *Thermococcus litoralis*), Hot Tub DNA polymerase derived from *Thermus flavus* and available from Amersham Corporation, and Tth DNA polymerase derived form *Thermus thermophilus*, available form Epicentre Technologies, Molecular Biology Resource Inc., or Perkin-Elmer Corp.

This method conducts the amplification using four pairs of oligonucleotide primers. A first set of four primers comprises four allele-specific primers which are unique with respect to each other. The four allele-specific primers are each paired with a common distant primer which anneals to the other DNA strand distant from the allele-specific primer. One of the allele-specific primers is complementary to the wild type allele (i.e., is allele-specific to the normal allele) while the others have a mismatch at the 3' terminal nucleotide of the primer. As noted, the four unique primers are individually paired for amplification (e.g., by PCR amplification) with a common distant primer. When the mutated allele is present, the primer pair including the allele-specific primer will amplify efficiently and yield a detectable product. While the mismatched primers may anneal, the strand will not be extended during amplification.

The above primer combination is useful where a mutation is known to exist at a single position on an allele of interest. Where the mutation may exist at one of two locations, eight pair of oligonucleotide primers may be used. The first set of four pair is as described above. The second four pair or primers comprises four allele-specific oligonucleotide primers complementary to the gene sequence contiguous with the site of the second possible mutation on the sense strand. These four primers differ at the terminal 3' nucleotide which is complementary to the wild type nucleotide or to one of the three possible mutations which can occur at this second known position. Each of the four allele-specific primers is paired with a single common distant primer which is complementary to the antisense strand upstream of the mutation.

During a PCR amplification using the above primers, only the primer which is fully complementary to the allele which is present will anneal and extend. The primers having a non-complementary nucleotide may partially anneal, but will not extend during the amplification process. Amplification generally is allowed to proceed for a suitable number of cycles, i.e., from about 20 to 40, and most preferably for about 30. This technique amplifies a mutation-containing fragment of the target gene with sufficient sensitivity to enable detection of the mutated target gene against a significant background of normal DNA.

The K-ras gene has point mutations which usually occur at one or two known positions in a known codon. Other oncogenes may have mutations at known but variable locations. Mutations with the K-ras gene are typically known to be associated with certain cancers such as adenocarcinomas of the lung, pancreas, and colon. FIGS. 1A through 2B illustrate a strategy for detecting, through PCR amplification, a mutation occurring at position 1 or 2 of the 12th codon of the K-ras oncogene. As previously noted, mutations at the first or second position of the 12th codon of K-ras are often associated with certain cancers such as adenocarcinomas of the lung, pancreas, and colon.

Figure 1B:
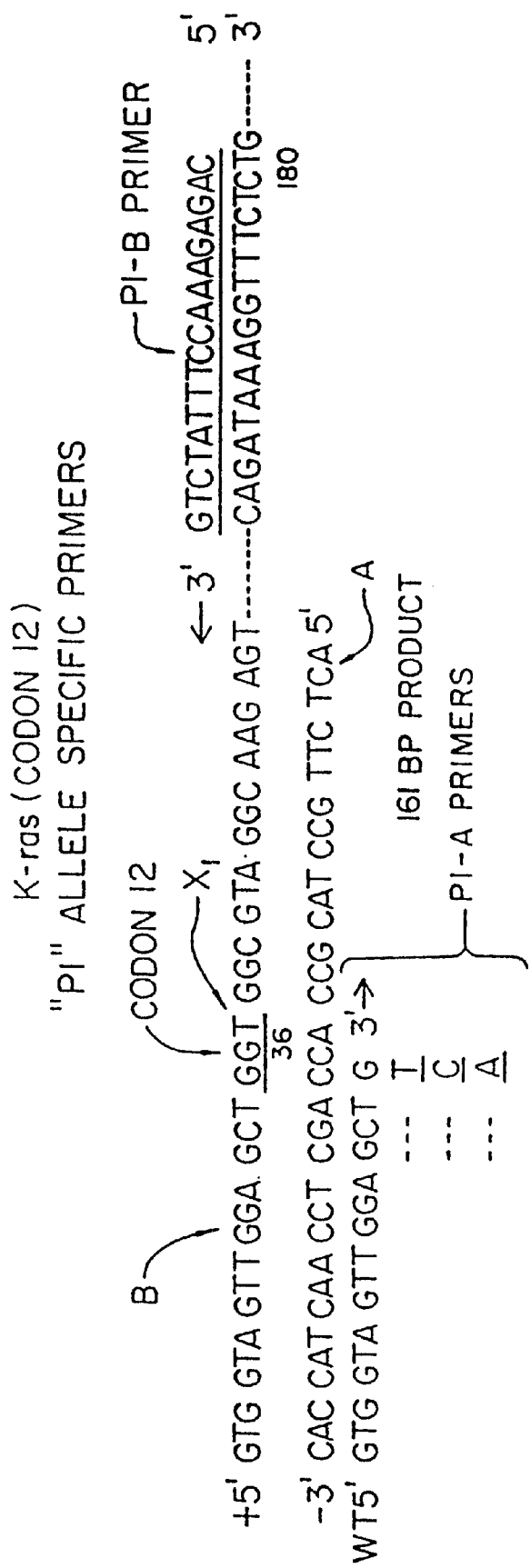

Referring to FIGS. 1A and 1B, the DNA from the patient sample is separated into two strands (A and B), which represent the sense and antisense strands. The DNA represents an oncogene having a point mutation which occurs on the same codon (i.e., codon 12) at position 1 ($X_1$). The allele-specific primers used to detect the mutation at position 1, include a set of four P1 sense primers (P1-A), each of which is unique with respect to the others. The four P1 -A primers are complementary to a gene sequence contiguous with the site of the mutation on strand A. The four P1-A primers preferably differ from each other only at the terminal 3' nucleotide which is complementary to the wild type nucleotide or to one of the three possible mutations which can occur at this known position. Only the P1-A primer which is fully complementary to the mutation-containing segment on the allele will anneal and extend during amplification.

A common downstream primer (P1-B), complementary to a segment of the B strand downstream with respect to the position of the P1-A primers, is used in combination with each of the P1-A primers. The P1-B primer illustrated in FIG. 1 anneals to the allele and is extended during the PCR. Together, the P1-A and P1-B primers identified in Table 1 and illustrated in FIG. 1B amplify a fragment of the oncogene having 161 base pairs.

Figure 2A:
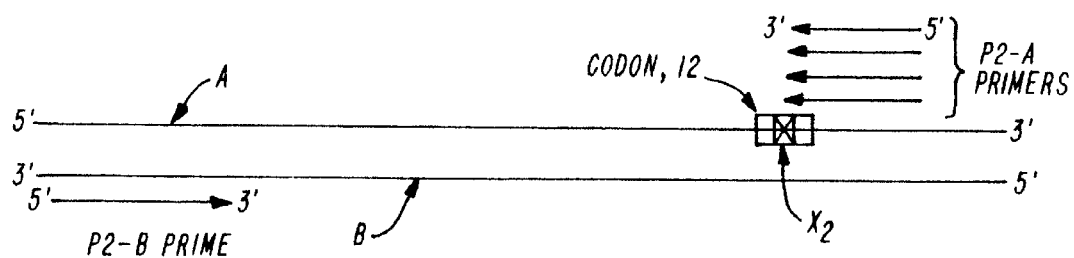
FIGS. 2A–2B are diagramatic representations of the amplification strategy for detection of a mutated K-ras gene with a mutation present at a second of two possible locations of K-ras.
Figure 2B:
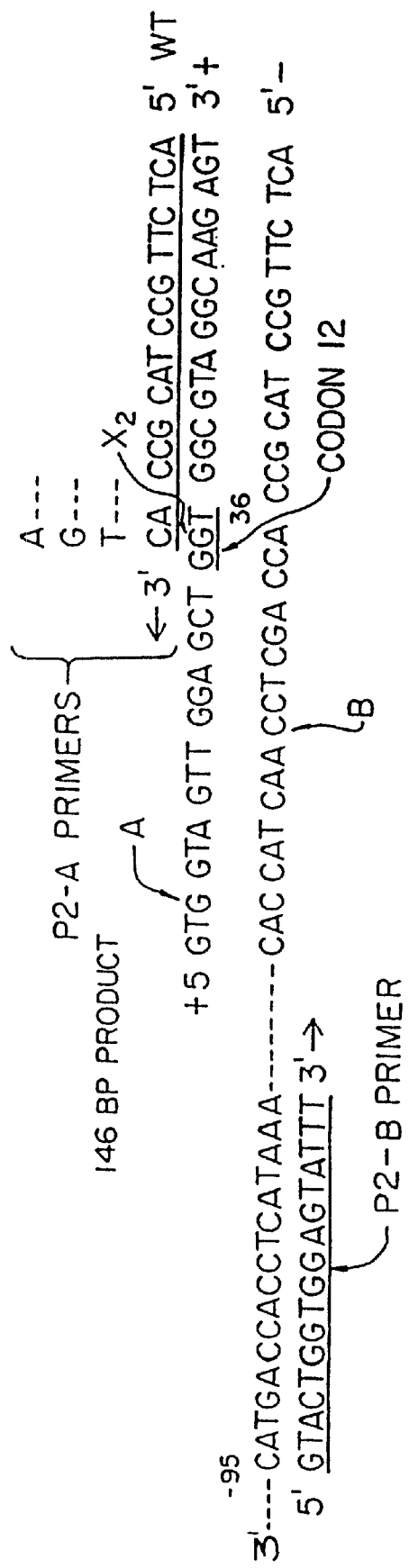

FIGS. 2A and 2B illustrate a scheme utilizing an additional set of four unique, allele-specific primers (P2-A) to detect a mutation which can occur at codon 12 of the oncogene, at position 2 ($X_2$). The amplification strategy illustrated in FIGS. 1A and 1B would be used in combination with that illustrated in FIGS. 2A and 2B to detect mutations at either position 1 ($X_1$) or position 2 ($X_2$) in codon 12.

Referring to FIGS. 2A and 2B, a set of four unique allele-specific primers (P2-A) are used to detect a mutation present at a position 2 ($X_2$) of codon 12. The four P2-A primers are complementary to the genetic sequence contiguous with the site of the second possible mutation. These four primers are unique with respect to each other and preferably differ only at the terminal 3' nucleotide which is complementary to the wild type nucleotide or to one of the three possible mutations which can occur at the second known position ($X_2$).

A single common upstream primer (P2-B) complementary to a segment of the A strand upstream of the mutation, is used in combination with each of the unique P2-A primers. The P2-A and P2-B primers identified in Table I and illustrated in FIG. 2B will amplify a fragment having 146 base pairs.

During the amplification procedure, the polymerase chain reaction is allowed to proceed for about 20 to 40 cycles and most preferably for 30 cycles. Following an initial denaturation period of about 5 minutes, each cycle, using the AmpliTaq DNA polymerase, typically includes about one minute of denaturation at 95° C., two minutes of primer annealing at about 58° C., and a one minute extension at 72° C. While the temperatures and cycle times noted above are currently preferred, it is noted that various modifications may be made. Indeed, the use of different DNA polymerases and/or different primers may necessitate changes in the amplification conditions. One skilled in the art will readily be able to optimize the amplification conditions.

Exemplary DNA primers which are useful in practicing the method of this invention to detect the K-ras gene, having point mutations at either the first or second position in codon 12 of the gene, are illustrated in Table I.

TABLE I

Primers Used to Amplify (by PCR) Position 1
and 2 Mutations at Codon 12 of K-ras Gene (5'-3')

| Sequence* | Strand | P1 or P2 |
|---|---|---|
| GTGGTAGTTGGAGCTG (SEQ ID NO:2) | A | P1 |
| GTGGTAGTTGGAGCTC (SEQ ID NO:3) | A | P1 |
| GTGGTAGTTGGAGCTT (SEQ ID NO:4) | A | P1 |
| GTGGTAGTTGGAGCTA (SEQ ID NO:5) | A | P1 |
| CAGAGAAACCTTTATCTG (SEQ ID NO:6) | B | P1 |
| ACTCTTGCCTACGCCAC (SEQ ID NO:7) | A | P2 |
| ACTCTTGCCTACGCCAG (SEQ ID NO:8) | A | P2 |
| ACTCTTGCCTACGCCAT (SEQ ID NO:9) | A | P2 |
| ACTCTTGCCTACGCCAA (SEQ ID NO:10) | A | P2 |
| GTACTGGTGGAGTATTT (SEQ ID NO:11) | B | P2 |

*Underlined bases denote mutations.

The primers illustrated in Table I are, of course, merely exemplary. Various modifications can be made to these primers as is understood by those having ordinary skill in the art. For example, the primers could be lengthened or shortened, however the 3' terminal nucleotides must remain the same. In addition, some mismatches 3 to 6 nucleotides back from the 3' end may be made and would not be likely to interfere with efficacy. The common primers can also be constructed differently so as to be complementary to a different site, yielding either a longer or shorter amplified product.

In one embodiment, the length of each allele-specific primer can be different, making it possible to combine multiple allele-specific primers with their common distant primer in the same PCR reaction. The length of the amplified product would be indicative of which allele-specific primer was being utilized with the amplification. The length of the amplified product would indicate which mutation was present in the specimen.

The primers illustrated in Table I and FIGS. 1B and 2B, and others which could be used, can be readily synthesized by one having ordinary skill in the art. For example, the preparation of similar primers has been described by Stork et al. (1991) *Oncogene*, 6:857–862.

Other amplification methods and strategies can also be utilized to detect gene sequences in biological fluids according to the method of the invention. For example, another approach would be to combine PCR and the ligase chain reaction (LCR). Since PCR amplifies faster than LCR and requires fewer copies of target DNA to initiate, one could use PCR as first step and then proceed to LCR. Primers such as the common primers used in the allele-specific amplification described previously which span a sequence of approximately 285 base pairs in length, more or less centered on codon 12 of K-ras, could be used to amplify this fragment, using standard PCR conditions. The amplified product (approximately a 285 base pair sequence) could then be used in a LCR or ligase detection reaction (LDR) in an allele-specific manner which would indicate if a mutation was present. Another, perhaps less sensitive, approach would be to use LCR or LDR for both amplification and allele-specific discrimination. The later reaction is advantageous in that it results in linear amplification. Thus the amount of amplified product is a reflection of the amount of target DNA in the original specimen and therefore permits quantitation.

LCR utilizes pairs of adjacent oligonucleotides which are complementary to the entire length of the target sequence (Barany F. (1991) *PNAS* 88:189–193; Barany F. (1991) *PCR Methods and Applications* 1:5–16). If the target sequence is perfectly complementary to the primers at the junction of these sequences, a DNA ligase will link the adjacent 3' and 5' terminal nucleotides forming a combined sequence. If a thermostable DNA ligase is used with thermal cycling, the combined sequence will be sequentially amplified. A single base mismatch at the junction of the oligonucleotides will preclude ligation and amplification. Thus, the process is allele-specific. Another set of oligonucleotides with 3' nucleotides specific for the mutant would be used in another reaction to identify the mutant allele. A series of standard conditions could be used to detect all possible mutations at any known site. LCR typically utilizes both strands of genomic DNA as targets for oligonucleotide hybridization with four primers, and the product is increased exponentially by repeated thermal cycling.

A variation of the reaction is the ligase detection reaction (LDR) which utilizes two adjacent oligonucleotides which are complementary to the target DNA and are similarly joined by DNA ligase (Barany F. (1991) *PNAS* 88:189–193). After multiple thermal cycles the product is amplified in a linear fashion. Thus the amount of the product of LDR reflects the amount of target DNA. Appropriate labeling of the primers allows detection of the amplified product in an allele-specific manner, as well as quantitation of the amount of original target DNA. One advantage of this type of reaction is that it allows quantitation through automation (Nickerson et al. (1990) *PNAS* 87: 8923–8927).

Examples of suitable oligonucleotides for use with LCR for allele-specific ligation and amplification to identify mutations at position 1 in codon 12 of the K-ras gene are illustrated below in Table II.

TABLE II

Oligonucleotides (5'-3') for use in LCR

| Sequence* | Strand | P1 or P2 |
|---|---|---|
| AGCTCCAACTACCACAAGTT (SEQ ID NO:12) | A1 | P1 |
| GCACTCTTGCCTACGCCACC (SEQ ID NO:13) | A2-A | P1 |
| GCACTCTTGCCTACGCCACA (SEQ ID NO:14) | A2-B | P1 |
| GCACTCTTGCCTACGCCACG (SEQ ID NO:15) | A2-C | P1 |
| GCACTCTTGCCTACGCCACT (SEQ ID NO:16) | A2-D | P1 |
| GGTGGCGTAGGCAAGAGTGC (SEQ ID NO:17) | B1 | P2 |
| AACTTGTGGTAGTTGGAGCT (SEQ ID NO:18) | B2-A | P2 |
| AACTTGTGGTAGTTGGAGCA (SEQ ID NO:19) | B2-B | P2 |
| AACTTGTGGTAGTTGGAGCC (SEQ ID NO:20) | B2-C | P2 |
| AACTTGTGGTAGTTGGAGCG (SEQ ID NO:21) | B2-D | P2 |

*Underlined bases denote mutations.

During an amplification procedure involving LCR four oligonucleotides are used at a time. For example, oligonucleotide A1 and, separately, each of the A2 oligonucleotides are paired on the sense strand. Also, oligonucleotide B1 and, separately, each of the B2 oligonucleotides are paired on the antisense strand. For an LCD procedure, two oligonucleotides are paired, i.e., A1 with each of the A2 oligonucleotides, for linear amplification of the normal and mutated target DNA sequence.

The method of the invention is applicable to the detection and quantitation of other oncogenes in DNA present in various biological fluids. The p53 gene is a gene for which convenient detection and quantitation could be useful because alterations in this gene are the most common genetic anomaly in human cancer, occurring in cancers of many histologic types arising from many anatomic sites. Mutations of the p53 may occur at multiple codons within the gene but 80% are localized within 4 conserved regions, or "hot spots", in exons 5, 6, 7 and 8. The most popular current method for identifying the mutations in p53 is a multistep procedure. It involves PCR amplification of exons 5–8 from genomic DNA, individually, in combination (i.e., multiplexing), or sometimes as units of more than one exon. An alternative approach is to isolate total cellular RNA, which is transcribed with reverse transcriptase. A portion of the reaction mixture is subjected directly to PCR to amplify the regions of p53 cDNA using a pair of appropriate oligonucleotides as primers. These two types of amplification are followed by single strand conformation polymorphism analysis (SSCP) which will identify amplified samples with point mutations from normal DNA by differences in mobility when electrophoresed in polyacrylamide gel. If a fragment is shown by SSCP to contain a mutation, the latter is amplified by asymmetric PCR and the sequence determined by the dideoxy-chain termination method (Murakami et al. (1991) Can. Res. 51: 3356–33612).

Further, the ligase chain reaction (LCR) may be useful with p53 since LCR is better able to evaluate multiple mutations at the same time. After determining the mutation, allele-specific primers can be prepared for subsequent quantitation of the mutated gene in the patient's plasma at multiple times during the clinical course.

Preferably, the method of the invention is conducted using biological fluid samples of approximately 5 ml. However, the method can also be practiced using smaller sample sizes in the event that specimen supply is limited. In such case, it may be advantageous to first amplify the DNA present in the sample using the common primers. Thereafter, amplification can proceed using the allele-specific primers.

The method of this invention may be embodied in diagnostic kits. Such kits may include reagents for the isolation of DNA as well as sets of primers used in the detection method, and reagents useful in the amplification. Among the reagents useful for the kit is a DNA polymerase used to effect the amplification and a PNA used to decrease false positives. Preferred polymerases are *Thermus aquaticus* DNA polymerase available from Perkin-Elmer as AmpliTaq DNA polymerase and AmpliTaq Stoffel fragment DNA polymerase. For quantitation of the mutated gene sequences, the kit can also contain samples of mutated DNA for positive controls as well as tubes for quantitation by competitive PCR having the engineered sequence in known amounts.

The quantitation of the mutated K-ras sequences can be achieved using either slot blot Southern hybridization or competitive PCR. Slot blot Southern hybridization can be a performed utilizing the allele-specific primers as probes under relatively stringent conditions as described by Verlaan-de Vries et al. (1986) Gene 50:313–20, 1986. The total DNA extracted from 5 ml of plasma will be slot blotted with 10 fold serial dilutions, followed by hybridization to an end-labeled allele-specific probe selected to be complementary to the known mutation in the particular patient's tumor DNA as determined previously by screening with the battery of allele-specific primers and PCR and LCR. Positive autoradiographic signals will be graded semiquantitatively by densitometry after comparison with a standard series of diluted DNA (1–500 ng) from tumor cell cultures which have the identical mutation in codon 12 of the K-ras, prepared as slot blots in the same way.

A modified competitive PCR (Gilliland et al. (1990) Proc. Nat. Acad. Sci., USA 87:2725:79; Gilliland et al., "Competitive PCR for Quantitation of mRNA", PCR Protocols (Acad. Press), pp. 60–69, 1990) could serve as a potentially more sensitive alternative to the slot blot Southern hybridization quantitation method. In this method of quantitation, the same pair or primers are utilized to amplify two DNA templates which compete with each other during the amplification process. One template is the sequence of interest in unknown amount, i.e. mutated K-ras, and the other is an engineered deletion mutant in known amount which, when amplified, yields a shorter product which can be distinguished from the amplified mutated K-ras sequence. Total DNA extracted from the plasma as described above will be quantitated utilizing slot blot Southern hybridization, utilizing a radiolabelled human repetitive sequence probe (BLUR8). This will allow a quantitation of total extracted plasma DNA so that the same amount can be used in each of the PCR reactions. DNA from each patient (100 ng) will be added to a PCR master mixture containing P1 or P2 allele-specific primers corresponding to the particular mutation previously identified for each patient in a total volume of 400 ml. Forty ml of master mixture containing 10 ng of plasma DNA will be added to each of 10 tubes containing 10 ml of competitive template ranging from 0.1 to 10 attomoles. Each reaction mixture will contain dNTPs (25 mM final concentration including [$\alpha$-$^{32}$P]dCTP at 50 mCi/ml), 50 pmoles of each primer, 2 mM MgCl$_2$, 2 units of *T. aquaticus* DNA polymerase, 1×PCR buffer, 50 mg/ml BSA, and water to a final volume of 40 ml. Thirty cycles of PCR will be followed by electrophoresis of the amplified products. Bands identified by ethidium bromide will excised, counted and a ratio of K-ras sequence to deletion mutant sequence calculated. To correct for difference in molecular weight, cpm obtained for genomic K-ras bands will multiplied by 141/161 or 126/146, depending upon whether position 1 (P1) or position 2 (P2) primers are used. (The exact ratio will depend upon the length of the deletion mutant.) Data will be plotted as log ratio of deletion template DNA/K-ras DNA vs. log input deletion template DNA (Gilliland et al. (1990) Proc. Nat. Acad Sci., USA 87:2725:79; Gilliland et al., "Competitive PCR for Quantitation of mRNA", PCR Protocols (Acad. Press), pp. 60–69, 1990).

A modified competitive PCR can also be developed in which one primer has a modified 5' end which carries a biotin moiety and the other primer has a 5' end with a fluorescent chromophore. The amplified product can then be separated from the reaction mixture by adsorption to avidin or streptavidin attached to a solid support. The amount of product formed in the PCR can be quantitated by measuring the amount of fluorescent primer incorporated into double-stranded DNA by denaturing the immobilized DNA by alkali and thus eluting the fluorescent single stands from the solid support and measuring the fluorescence (Landgraf et al. (1991) Anal. Biochem. 182:231–235, 1991).

The competitive template comprises derived deletion mutants with a sequence comparable to the fragments of the wild-type K-ras and the mutated K-ras gene amplified by the P1 and P2 series of primers described herein, except that there is an internal deletion of 10 nucleotides. Therefore, the amplified products are smaller, i.e., 54 and 52 nucleotides, respectively. Thus, the same primers can be used and yet amplified products from the derived mutants can be readily distinguished from the amplified genomic sequences.

Seven deletion templates are produced using PCR. The starting material is the 52-mer or the 54-mer oligonucleotides synthesized by Operon (Operon Technologies, Alameda, Calif.) which contain the same sequences as the 62-mer or 64-mer sequences amplified by the allele-specific amplification with the P2 or P1 primers, respectively, except that there are 10 nucleotides deleted from the middle. There are seven variations of this oligonucleotide which contain the wild-type sequence of codon 12, as well as each of the three mutations which can occur in P1 or P2 of this codon. First position codon 12 mutations include G→A (e.g., with A549 tumor DNA), G→T (e.g., with Calu1 and PR371 tumor DNA), and G→C (e.g., with A2182 and A1698 tumor DNA). Second position codon 12 mutations include G→A (e.g., with Aspc1 tumor DNA), G→T (e.g., with SW480 tumor DNA), and G→C (e.g., with 818-1, 181-4, and 818-7 tumor DNA). G→T transversions in the first or second position account for approximately 80% of the point mutations found in pulmonary carcinoma and GAT (aspartic acid) or GTT (valine) are most common in pancreatic cancer.

In summary, the P1 and P2 primers are used in an allele-specific manner with the 54-mer with the normal sequence and with the 52-mer or 54-mer containing each specific mutation. These deletion mutants are amplified, using the same allele-specific primers used for amplifying the genomic DNA. The seven oligonucleotides are individually amplified by PCR utilizing the four P1 primers and the three P2 primers each paired with the respective L1 or L2 primers. The template generated by the wild-type P1 primer can also be used as template for the wild-type P2 reaction. Thus, a separate wild-type template utilizing wild-type P2 primer need not be generated. This procedure generates seven batches of 52 nucleotide or 54 nucleotide double-stranded template which can be used in subsequent competitive PCR. Each of the amplified products is gel purified and the DNA is quantitated by spectrophotometry. Subsequently, each of the seven amplification products is sequenced to confirm its authenticity. Each double-stranded template is sequenced with both the common primer (L1 or L2) and the complementary allele-specific amplification primer in order to attain the entire 52 nucleotide or 54 nucleotide sequences. Subsequently, the shorter templates can be used in known serial dilutions in a competitive PCR as outlined above.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example I

Isolation of Soluble DNA from Blood

Blood was collected in 13×75 mm vacutainer tubes containing 0.05 ml of 15% K$_3$EDTA. The tubes were immediately centrifuged at 4° C. for 30 minutes at 1000 g, the plasma was removed and recentrifuged at 4° C. for another 30 minutes at 1000 g. The plasma was stored at −70° C. Next, DNA was deproteinized by adding an equal volume of 20% NaCl to 5 ml aliquots of plasma which were then boiled for 3 to 4 minutes. After cooling, the samples were centrifuged at 3000 rpm for 30 minutes. The supernatant was removed and dialysed against three changes of 10 mM Tris-HCl (pH 7.5)/1 mM EDTA (pH 8.0) ("TE") for 18 to 24 hours at 4° C. The DNA was extracted once with two volumes of phenol, 2×1 volume phenol:chloroform:isoamyl alcohol (25:24:1) and 2×1 volume chloroform: isoamyl alcohol (24:1). DNA was subsequently precipitated with NaCl at 0.3M, 20 mg/ml glycogen as a carrier and 2.5 volumes of 100% ethanol at minus 20° C. for 24 hours. DNA was recovered by centrifugation in an Eppendorf Centrifuge at 4° C. for 30 minutes. The DNA was then resuspended in a TE buffer. The DNA extracted and prepared in the above manner was then able to be amplified.

Example II

Isolation of Soluble DNA from Urine

Urine samples from patients with pancreatic cancer was collected and subject to centrifugation for 10 minutes at 3000 rpm in a Beckman TJ6 centrifuge to remove cell debris. To sterilize the urine, the samples were then boiled for 10 minutes and allowed to cool to room temperature. Precipitates were removed via centrifugation. Five hundred $\mu$l of Proteinase K was then added to all samples and the samples were incubated overnight at 55° C. The samples were then dialyzed against two changes of 4 liters of water in a cold room (4 hours each or overnight). The samples were then boiled to inactivate the Proteinase K, the pH measured and adjusted to 7.4.

The samples were the loaded on elutips (with prefilters), the elutips washed with 1 ml 20 mM Low Salt Buffer at a rate of not more than 1 ml/mn. The elutips were then equilibrated with High Salt Buffer for 15 minutes at 37° C. and eluted with 500 $\mu$l HSB at a rate of not more than 0.5 ml/min. The eluates were centrifuged through 30,000 NMWL filters to concentrate them to around 50 $\mu$l. The concentrate was then washed with 6 changes of 300 $\mu$l water and diluted with 120 $\mu$l of water and the OD$_{260/280}$ of 20 $\mu$l diluted with 80 $\mu$l of water is measured. Following isolation of the DNA from urine. Mutant alleles in the urine can be detected using the methods described herein.

Example III

Amplification of DNA Isolated from Blood

An allele-specific amplification of DNA obtained and prepared according to Example I was conducted by PCR as follows to detect the K-ras gene in the DNA having a mutation at position 1 or 2 of the codon 12 of the K-ras gene. In each of eight reaction tubes was added DNA extracted from 0.5 ml of plasma in total volume of 40 ml containing 67 mM Tris-HCl (pH 8.8), 10 mM β-mercaptoethanol, 16.6 mM ammonium sulfate, 6.7 mM EDTA, 2.0 mM, MgCl$_2$, 50 mg/ml BSA, 25 mM dNTP. Also, 50 pmoles of each of the primers identified in Table I was included, together with 3 units of *Thermus aquaticus* DNA polymerase (available from Perkin-Elmer as AmpliTaq). PCR was conducted with an initial denaturation at 95° C. for 5 minutes, followed by 30 cycles of PCR amplification in a DNA thermal cycler (Cetus; Perkin-Elmer Corp. Norwalk, Conn.). Each amplification cycle includes a 1 minute denaturation at 95° C., a 2 minute primer annealing period at 58° C., and a 1 minute extension period at 72° C.

Following the completion of amplification, 10–15 ml of each of the PCR reaction products is analyzed by electrophoresis in a 2% agarose gel/1×TAE-0.5 mg/ml EtBr. The electrophoresis uses an applied voltage of 100 volts for 90 minutes. Photographs of the samples are then taken using ultraviolet light under standard conditions.

Example IV

Amplification of Plasma DNA in the Presence of Peptide Nucleic Acid

Isolation of Soluble DNA from Plasma:

DNA was isolated from 200 μl plasma from the blood of patients with pancreatic cancer using Qiagen's QIAamp Blood Kit as follows:

Two hundred μl of plasma was placed in a 1.5 ml microfuge tube. Twenty-five μl of Qiagen protease and 200 μl of buffer AL (40 parts Reagent AL2+160 parts Reagent AL1) were then added to the tube and the contents mixed. The tube was then incubated at 70° C. for 10 minutes. Two hundred and ten μl of EtOH was added to the tube and the contents mixed. The plasma mixture was then placed in a QIAamp spin column and centrifuged at 6000×g (8000 rpm) for 1 minute. The QIAamp spin column was then placed in a clean collection tube and 500 μl of Buffer AW was added. The column was then centrifuged again at 6000×g (8000 rpm) for 1 minute. The QIAamp spin column was again placed in a clean collection tube and another 500 μl of Buffer AW was added. The column was centrifuged at 6000×g (8000 rpm) for 1 minute and at full speed for a further 2 minutes. The QIAamp spin column was then placed in a clean 1.5 ml microfuge tube and the DNA eluted with 200 μl dH$_2$O or 10 mM Tris-HCl, pH 9.0 preheated to 70° C. The microfuge tube holding the QIAamp spin column was then centrifuged at 6000×g (8000 rpm) for 1 minute. The plasma DNA was then in a total volume of 200 μl.

Strand Displacement:

Prior to strand displacement, the DNA was concentrated to a volume of 20 μl or less on a Millipore Ultrafree-MC (30,000 MWCO) filter unit. The plasma DNA was added to a 0.5 μl microfuge tube together with 1 μM peptide nucleic acid (PNA) (H-GCC-TAC-GCC-ACC-AGC-TCC-AA-NH$_2$) (SEQ ID NO:1), qs to a total volume of 20 μl with 10/1 TE, pH 7.5 (10 mM Tris-HCl, pH 7.5/1 mM EDTA). The mixture was then incubated for 1 hour at 37° C.

Spanning K-ras PCR Amplification of DNA:

The 20 μl of the strand-displaced, plasma DNA was then mixed with 20 μl of PCR master mix (4 units AmpliTAQ DNA polymerase Stoffel fragment, 1×PCR Stoffel buffer, 2 mM MgCl$_2$, 50 μM each dNTP, 1 μM L2 K-ras spanning primer (5' GCC-TGC-TGA-AAA-TGA-CTG-AA 3') (SEQ ID NO:22), 1 μM CP-PNA 1 spanning primer (5'CAT-CCG-TTC-TCA-CGG-AAC-TGC-TAT-GTC-GAT 3') (SEQ ID NO:23), 1 μM PNA, 50 μg/ml BSA, qs to 20 μl dH20.) The PCR cycling conditions were as follows: the initial denaturation was performed for 5 minutes at 94° C. followed by 30 cycles at: 94° C. for 1 minute (denature), 75° C. for 30 seconds (PNA anneal), 65° C. for 1 minute (primer anneal), and 70° C. for 1 minute (extension).

Allele-Specific PCR Amplification:

The strand displaced, common amplified DNA was diluted 1:10K to be used in an allele-specific PCR. The PCR Maser mix included: 4 units AmpliTAQ DNA polymerase Stoffel fragment, 1×PCR Stoffel buffer, 2 mM MgCl$_2$, 5 μM each dNTP, 1 μM common primer for position 1 or position 2 of codon 12 of K-ras (L1 (5' TAT-GTC-GAT-TAA-GTC-TTA-GT 3') (SEQ ID NO:24) or L2 (5' GCC-TGC-TGA-AAA-TGA-CTG-AA 3') (SEQ ID NO:22), 1 μM allele-specific primer for position 1 or position 2 of codon 12 of K-ras, and 50 μg/ml BSA. The DNA was then amplified under the following cycling conditions: the initial denaturation was performed for 5 minutes at 94° C. followed by 30 cycles at: 94° C. for 1 minute (denature), 60° C. for 1 minute (primer anneal), 72° C. for 1 minute (extension), and 72° C. for 7 minutes (final extension). The DNA was analyzed on a 3.5% agarose gel in 1×TBE/0.5 μg/ml of ethidium bromide. The K-ras position 2 product was 62 bp and the K-ras position 1 was 64 bp.

Several experiments were performed using the above-described methods with the following variations: *Experiment A*

Figure 3:
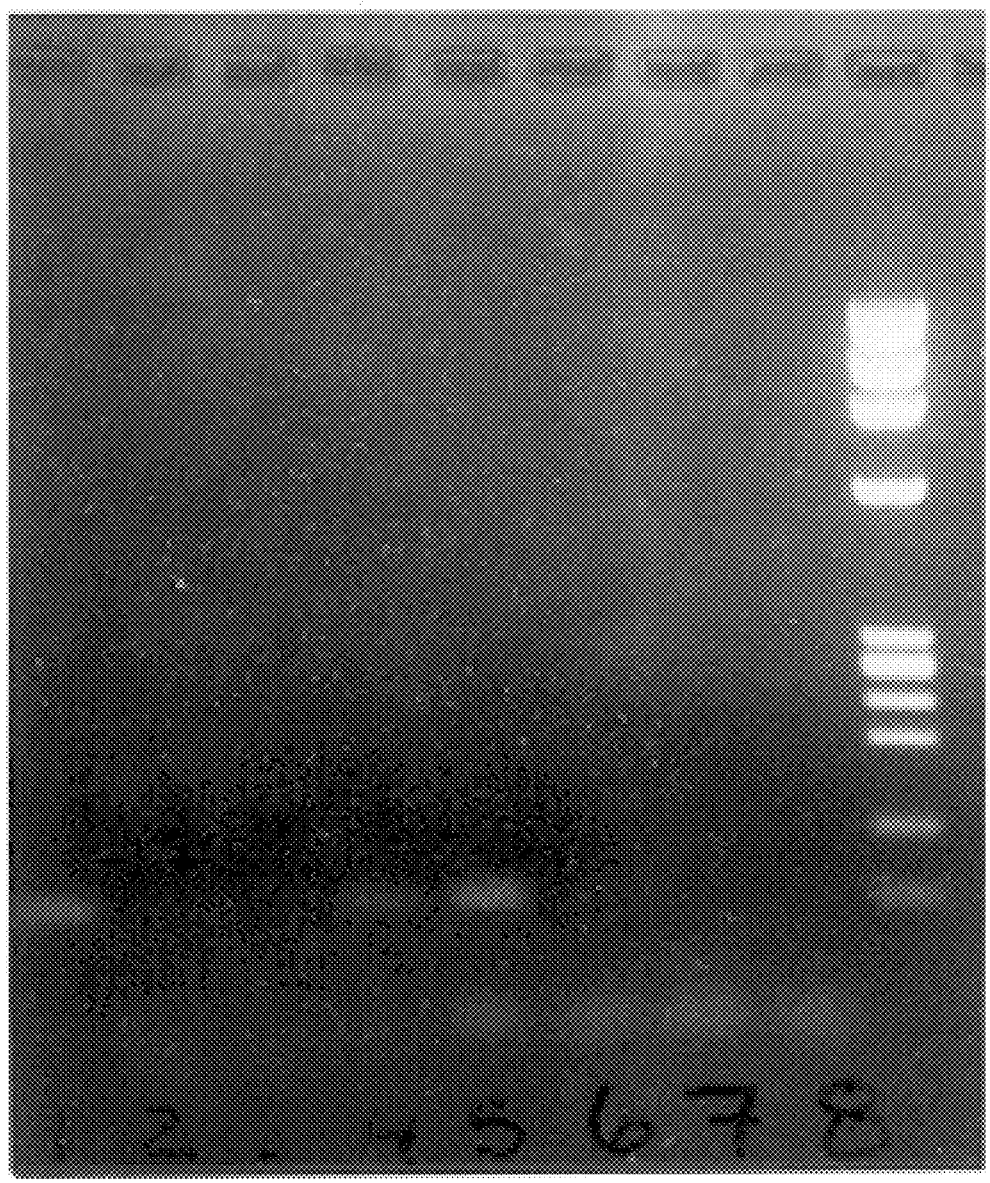
FIG. 3 is a photograph of an agarose gel which shows allele-specific amplification of 200 ng wild-type DNA without prior PNA strand displacement and without PNA in the common amplification of the DNA.

Amplification of Wild-Type DNA (10 ng) Without PNA Strand Displacement or PNA in the Spanning K-ras PCR Amplifications Allele-specific amplification of 200 ng wild-type DNA was performed as described above. The resulting amplification products were analyzed by agarose gel electrophoresis as described above. The allele-specific amplification step was not preceded by a PNA strand displacement step. The results of this experiment are illustrated in FIG. 3. Lanes 1–4 include 1:10K dilution of the common amplified DNA in an allele-specific amplification with K-ras position 2 primers 2C (lane 1) (wild-type), 2A (lane 2), 2G (lane 3), 2T (lane 3) (false positive). Lanes 5–8 include K-ras position 1 primers 1G (lane 5) (wild-type), 1A (lane 6), 1C (lane 7), and 1T (lane 8). As shown in Experiment B, if 10 ng of wild-type DNA is used, the results are the same but the product bands are very faint. (compare FIG. 3 with FIG. 4). *Experiment B*

Figure 4:
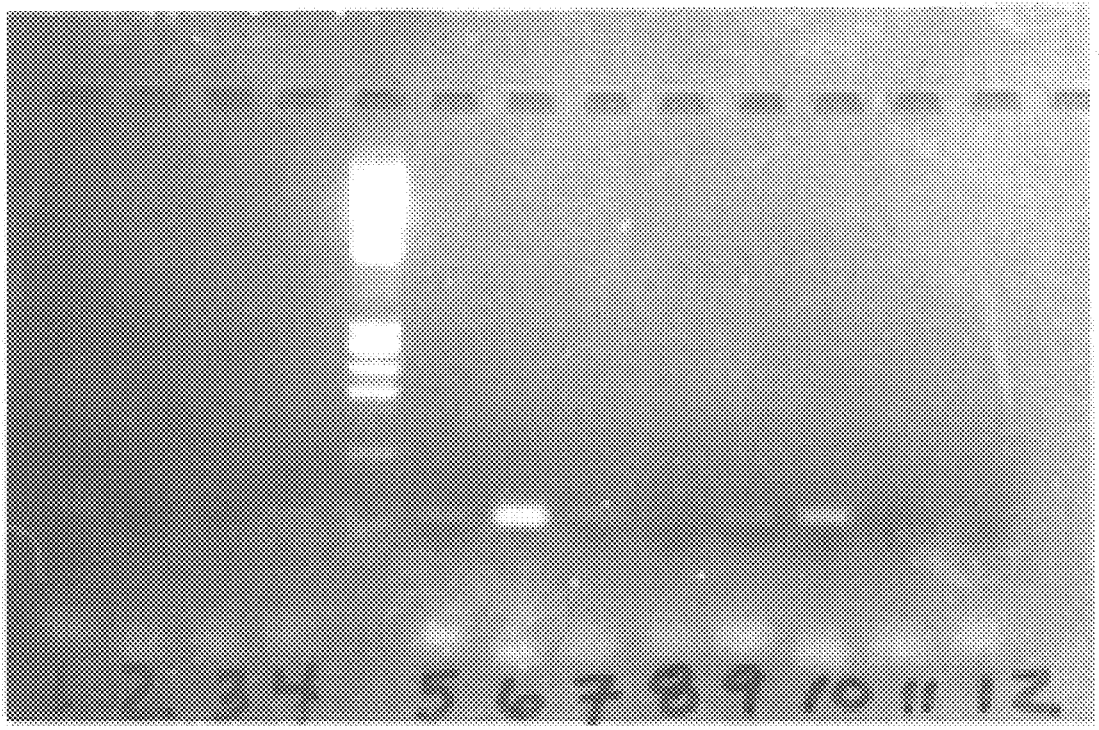
FIG. 4 is a photograph of an agarose gel which shows allele-specific amplification of 10 ng wild-type DNA and 10 pg and 100 ng of mutated DNA without prior PNA strand displacement and without PNA in the common amplification of the DNA.

Amplification of Wild-Type DNA (10 ng) and Mutated DNA (10 ng and 100 pg) Without PNA Strand Displacement or PNA in the Spanning K-ras PCR Amplifications Amplification of 10 ng wild-type DNA, 10 ng and 100 pg of mutated DNA was performed as described above. The resulting amplification products were analyzed by agarose gel electrophoresis as described above. The allele-specific amplification step was not preceded by a PNA strand displacement step. There was a spanning K-ras PCR amplification step without PNA. A 1:10,000 dilution of these PCR products was used in an allele-specific PCR amplification. The results of this experiment are illustrated in FIG. 4. Lanes 1–4 show products from from 10 ng wild-type DNA with K-ras position 2 primers 2C (wild-type-lane 1), 2A (lane 2), 2G (lane 3), and 2T (lane 4) (false positives). Lanes 5–8 show products from 10 ng mutated DNA (GTT) with K-ras position 2 primers 2C (lane 5) (false positive), 2A (lane 6) (mutated), 2G (lane 7) (false positive), and 2T (lane 8) (false positive). Lanes 9–12 show products from 100 pg mutated DNA (GGT) with K-ras position 2 primers 2C (lane 9) (false positive), 2A (lane 10) (mutated), 2G, and 2T (lanes 11 and 12) (false positive).

Experiment C

Figure 5:
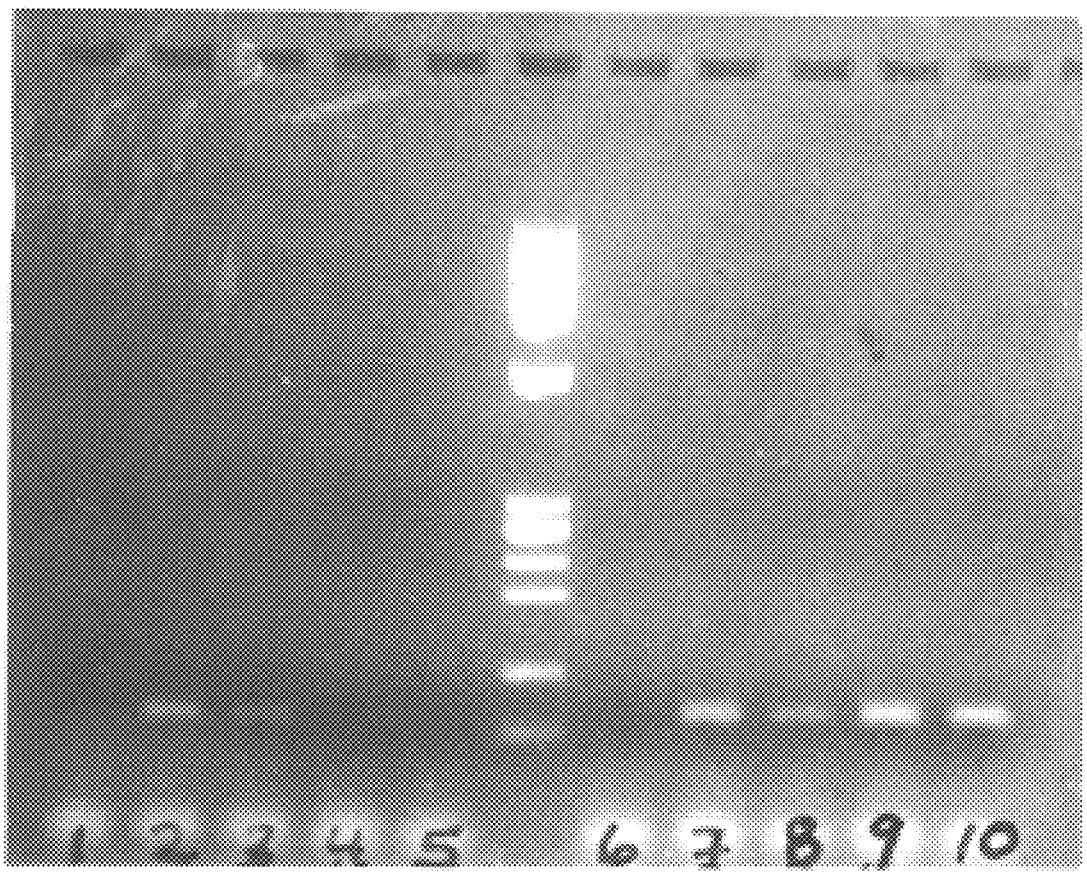
FIG. 5 is a photograph of an agarose gel which shows amplification of wild-type DNA, mutated DNA, and a mixture of wild-type and mutated DNA with PNA strand displacement, with and without PNA in the common amplification of the DNA.

Amplification of Wild-Type DNA, Mutated DNA, and a Mixture of Wild-Type and Mutated DNA With PNA Strand Displacement and With and Without PNA in the Spanning K-ras PCR Amplification Allele-specific amplification of wild-type, mutated DNA and a mixture of wild-type and mutated DNA was performed as described above. The resulting amplification products were analyzed by agarose gel electrophoresis as described above. As described above, the allele-specific amplification step was preceded by a PNA strand displacement step and/or a spanning K-ras PCR/PNA amplification step. The results of this experiment are summarized in Table III and illustrated in FIG. 5.

TABLE III

| Lane | sample* | PNA Strand Displacement | PNA in Spanning PCR | Product Detection |
|---|---|---|---|---|
| 1 | 10 ng WT | + | + | − |
| 2 | 10 ng mutated | + | + | +++ |
| 3 | 5 ng WT + 5 ng mutated | + | + | + |
| 4 | 10 ng WT | − | + | − |
| 5 | 10 ng WT | − | + | − |
| 6 | 10 ng WT | + | − | − |
| 7 | 10 ng mutated | + | − | +++ |
| 8 | 5 ng WT + 5 ng mutated | + | − | + |
| 9 | 10 ng WT | − | − | + |
| 10 | 10 ng WT | − | − | + |

*WT = wild-type

The results from this experiment demonstrate that either PNA strand displacement or clamping in the spanning PCR amplification is effective in inhibiting PCR amplification of wild-type in the spanning PCR amplification. PNA strand displacement of the wild-type sequence of K-ras efficiently blocks the amplification of wild-type K-ras with or without addition of PNA during the spanning K-ras PCR (lanes 1 and 6 of FIG. 5). The mutated K-ras sequence was not affected by the wild-type PNA (lanes 2, 3, 7, and 8 of FIG. 5).
*Experiment D*

Figure 6:
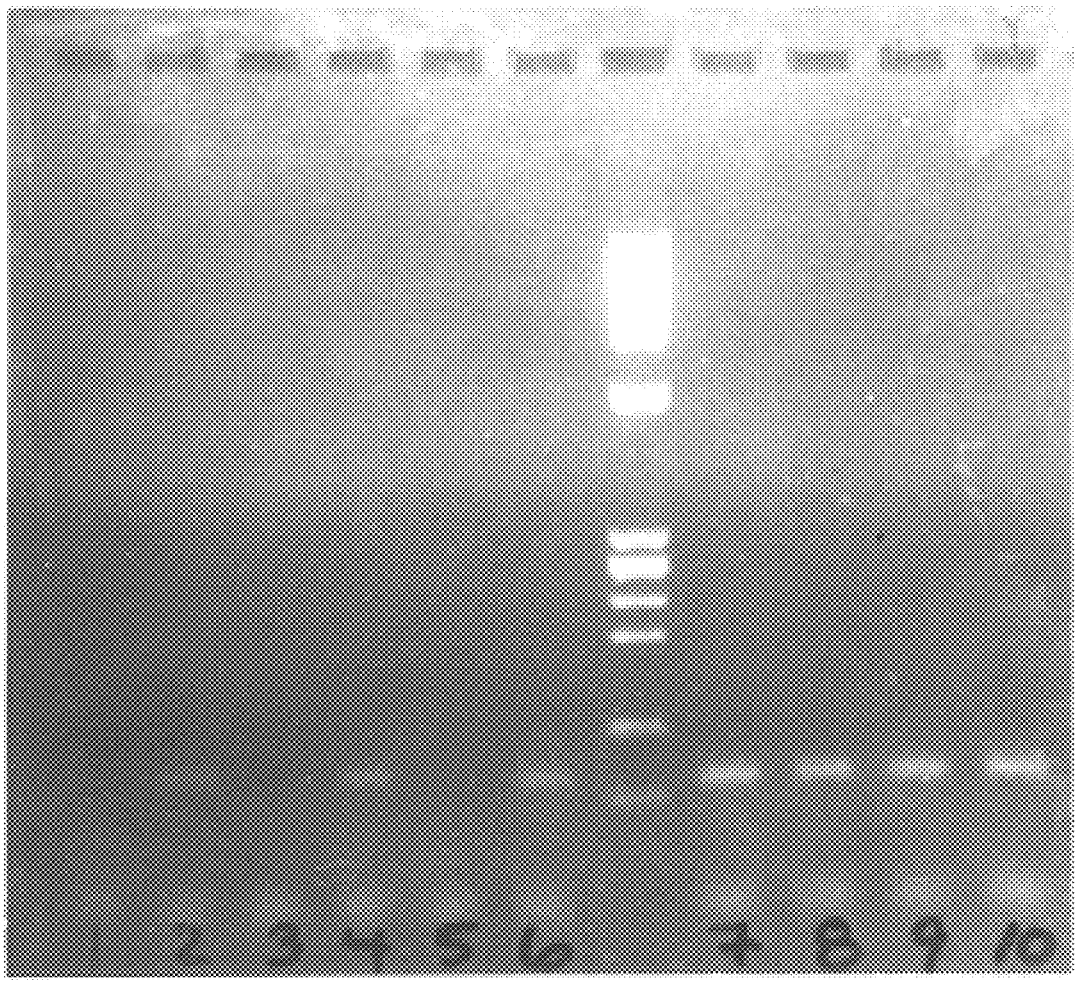
FIG. 6 is a photograph of an agarose gel which shows allele-specific amplification of wild-type DNA and a mixture of wild-type and mutated DNA with PNA strand displacement and with PNA in the common amplification of the DNA.

Amplification of Wild-Type DNA and a Mixture of Wild-Type DNA and Mutated DNA With PNA Strand Displacement and PNA in the Spanning K-ras PCR Amplification Ten ng of wild-type DNA and a mixture of 5 ng wild-type DNA and 5 ng mutated DNA were subject to strand displacement with 1 μM PNA under a variety of pH conditions (pH 5.5, pH 6.5, and pH 7.5). The DNA was then amplified using an additional 1 μM PNA and the spanning K-ras primers described above. The results of this experiment are illustrated in FIG. 6. Lanes 1, 3, and 5 include 10 ng wild-type DNA with PNA. Lanes 2, 4, and 6 include 5 ng wild-type DNA and 5 ng mutated DNA with PNA. There is no product in the wild-type lanes (i.e., lanes 1, 3, and 5), indicating that the PNA inhibited the amplification of the wild-type sequence. In the lanes with the mixed wild-type and mutated DNA, the product band results from the amplification of the mutated DNA (i.e., lanes 2, 4, and 6). Lanes 8–11 represent wild-type DNA amplified without the addition of PNA indicating that without PNA, a product is formed. *Experiment E*

Figure 7:
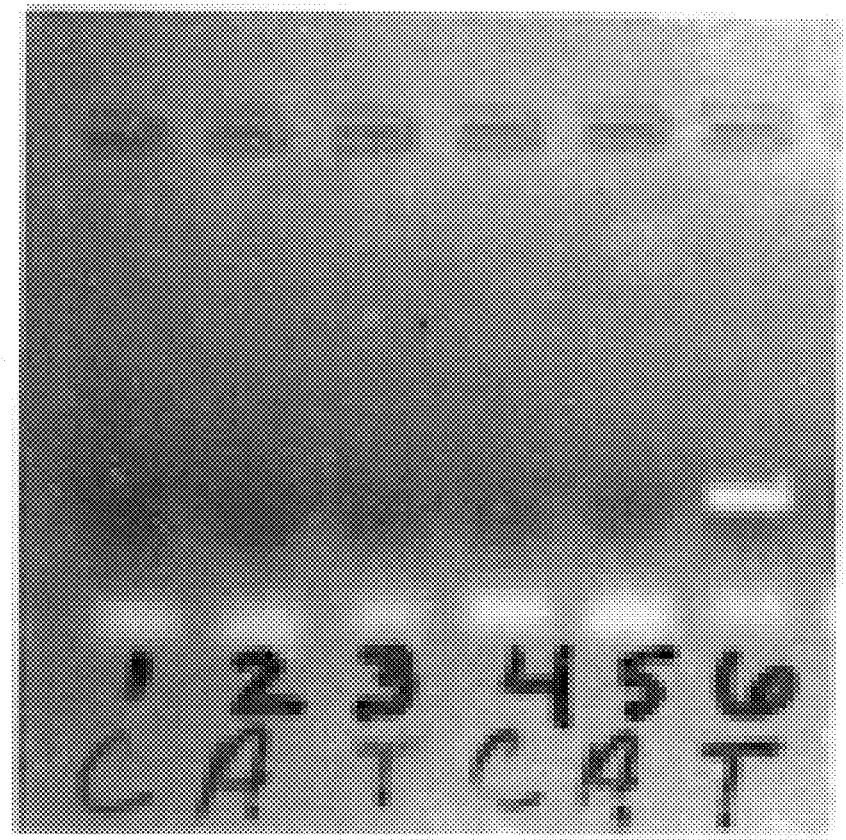
FIG. 7 is a photograph of an agarose gel which shows allele-specific amplification of wild-type DNA and a mixture of wild-type and mutated DNA with PNA strand displacement and with PNA in the common amplification of the DNA.

Amplification of Wild-Type DNA and a Mixture of Wild-Type DNA and Mutated DNA With PNA Strand Displacement and PNA in the Spanning K-ras PCR Amplification Amplification of 10 ng of wild-type DNA and a mixture of 5 ng of mutated DNA and 5 ng of wild-type DNA was performed as described above. A 1:10,000 dilution of the PCR products was used in an allele-specific PCR amplification. The resulting amplification products were analyzed by agarose gel electrophoresis as described above. The results of this experiment are illustrated in FIG. 7. Lanes 1–3 include wild-type DNA with K-ras position 2 primer 2C (lane 1) (wild-type), 2A (lane 2), 2T (lane 3). Lanes 4–6 include a mixture of wild-type and mutated DNA (GAT) with K-ras position 2 primer 2C (lane 4), 2A (lane 5), and 2T (lane 6) (mutated). As these results demonstrate, the use of PNA in the strand displacement step and in the first PCR eliminates the false positive reaction in the allele-specific amplification step.
Equivalents Those skilled in the art will recognize, or be able to ascertain using no more than routine experimentation, many equivalents of the specific embodiments of the invention described herein. Such equivalents are intended to be encompassed by the following claims.

I claim:

1. A method of detecting a mutant allele, comprising the steps of:
providing a sample of a biological fluid containing soluble DNA, including a mutant allele of interest;
extracting the DNA from the sample;
contacting the DNA with a peptide nucleic acid which is complementary to a segment of a strand of the DNA;
amplifying the mutant allele of interest in an allele-specific manner using at least a first set of four allele-specific oligonucleotide primers having one primer the 3' terminal nucleotide of which is complementary to a mutation-containing segment on a first strand of the DNA and a first common primer for pairing during amplification to each allele-specific primer, the common primer being complementary to a segment of a second strand of the DNA at a distance from the position of the first primer such that the mutant allele of interest is amplified; and
detecting the presence of the mutant allele of interest.

2. The method of claim 1 further comprising the step of amplifying the DNA in the presence of a peptide nucleic acid which is complementary to a segment of the DNA before the step of amplifying the mutant allele of interest.

3. The method of claim 1 further comprising the step of removing protein from the sample and inactivating any DNase within the sample before the step of extracting the DNA.

4. The method of claim 3, wherein the mutant allele is amplified in an allele-specific manner using the polymerase chain reaction (PCR).

5. The method of claim 4, wherein following the amplification step, the step of detecting the presence of the mutant allele of interest comprises performing an allele-specific ligase chain reaction (LCR) or a ligase detection reaction (LDR) using the amplified product of PCR.

6. The method of claim 3 wherein protein is removed and DNases are inactivated by adding a salt solution to the sample and subsequently boiling the sample.

7. The method of claim 3 wherein the biological fluid is selected from the group consisting of whole blood, serum, plasma, urine, sputum, colonic effluent, fluid from endoscopic retrograde cholangeopancreatography, bone marrow, lymph, and cerebrospinal fluid.

8. The method of claim 3 wherein the mutant allele comprises a gene sequence having a point mutation at a known location.

9. The method of claim 8 wherein the first DNA strand is the sense strand and the second DNA strand is the antisense strand.

10. The method of claim 3 wherein the step of amplifying the mutant allele with the PCR is conducted using a DNA polymerase which lacks the 3' exonuclease activity and therefore the ability to repair single nucleotide mismatches at the 3' end of the primer.

11. The method of claim 10 wherein the DNA polymerase is a *Thermus aquaticus* DNA polymerase.

12. The method of claim 10 wherein the first set of allele-specific oligonucleotide primers comprises:
four sense primers, one of which has a 3' terminal nucleotide complementary to a point mutation of the sense strand, and the remaining three of which are complementary to the wild type sequence for the segment to be amplified and to sequences having the remaining two possible mutations at the mutated point of the sense strand; and
a common antisense primer complementary to a segment of the antisense strand distant from the location on the sense strand at which the sense primers will anneal, the common antisense primer being paired with each of the sense primers during amplification.

13. The method of claim 12 wherein the 3' terminal nucleotide of the complementary sense primer anneals with the mutated nucleotide of the sense strand.

14. The method of claim 4 wherein the mutant allele comprises a gene sequence having a point mutation at one of two known locations.

15. The method of claim 14 wherein the step of amplifying the mutant allele through the PCR further comprises the use of a second set of four allele-specific oligonucleotide primers, in conjunction with the first set, wherein the second set of allele-specific oligonucleotide primers comprises:
four sense primers, one of which has a 3' terminal nucleotide complementary to a point mutation of the sense strand, and the remaining three of which are complementary to the wild type sequence for the segment to be amplified and sequences having the remaining two possible mutations at the mutated point of the sense strand; and
a common antisense primer complementary to a segment of the antisense strand distant from the location on the sense strand at which the sense primers will anneal, the common antisense primer being paired with each of the sense primers during amplification.

16. The method of claim 15 wherein the 3' terminal nucleotide of the complementary sense primer anneals with the mutated nucleotide of the sense strand.

17. The method of claim 16 wherein the mutant allele to be detected is the K-ras gene sequence having a mutation at position 1 or 2 in the twelfth codon.

18. The method of claim 17 wherein the first set of allele-specific oligonucleotide primers comprises sense primers having the following sequences

| | |
|---|---|
| 5'GTGGTAGTTGGAGCTG 3' (wild type) | (SEQ ID NO:2) |
| 5'GTGGTAGTTGGAGCTC 3' | (SEQ ID NO:3) |
| 5'GTGGTAGTTGGAGCTT 3' | (SEQ ID NO:4) |
| 5'GTGGTAGTTGGAGCTA 3' | (SEQ ID NO:5) | and the common antisense primer having the following sequence

| | |
|---|---|
| 5'CAGAGAAACCTTTATCTG 3' | (SEQ ID NO:6). |

19. The method of claim 15 wherein the second set of allele-specific oligonucleotide primers comprises sense primers having the following sequences

| | |
|---|---|
| 5'ACTCTTGCCTACGCCAC 3' (wild type) | (SEQ ID NO:7) |
| 5'ACTCTTGCCTACGCCAG 3' | (SEQ ID NO:8) |
| 5'ACTCTTGCCTACGCCAT 3' | (SEQ ID NO:9) |
| 5'ACTCTTGCCTACGCCAA 3' | (SEQ ID NO:10) | and the common antisense primer having the following sequence

| | |
|---|---|
| 5'GTACTGGTGGAGTATTT 3' | (SEQ ID NO:11). |

20. The method of claim 3 wherein the step of detecting the presence of amplified DNA is conducted by gel electrophoresis in 1–5% agarose gel.

21. The method of claim 3 wherein the biological fluid is selected from the group consisting of whole blood, serum, plasma, urine, sputum, colonic effluent, fluid from endoscopic retrograde cholangeopancreatography, bone marrow, lymph, and cerebrospinal fluid.

22. A diagnostic kit for detecting the presence of a mutated K-ras gene sequence in biological fluid, wherein the mutation is present in the twelfth codon at position 1, comprising:

reagents to facilitate the deproteinization and isolation of DNA;

reagents to facilitate amplification by PCR which include a peptide nucleic acid which is complementary to a segment of a strand of the DNA;

a heat stable DNA polymerase; and a first set of allele-specific oligonucleotide sense primers having the following sequences

| | |
|---|---|
| 5'GTGGTAGTTGGAGCTG 3' | (SEQ ID NO:2) |
| 5'GTGGTAGTTGGAGCTC 3' | (SEQ ID NO:3) |
| 5'GTGGTAGTTGGAGCTT 3' | (SEQ ID NO:4) |
| 5'GTGGTAGTTGGAGCTA 3' | (SEQ ID NO:5) | and a first common antisense primer having the following sequence

| | |
|---|---|
| 5'CAGAGAAACCTTTATCTG '3 | (SEQ ID NO:6). |

23. The diagnostic kit of claim 22 further comprising a second set of allele-specific oligonucleotide sense primers having the following sequences

| | |
|---|---|
| 5'ACTCTTGCCTACGCCAC 3' | (SEQ ID NO:7) |
| 5'ACTCTTGCCTACGCCAG 3' | (SEQ ID NO:8) |
| 5'ACTCTTGCCTACGCCAT 3' | (SEQ ID NO:9) |
| 5'ACTCTTGCCTACGCCAA 3' | (SEQ ID NO:10) | and a second common antisense primer having the following sequence

| | |
|---|---|
| 5'GTACTGGTGGAGTATTT 3' | (SEQ ID NO:11) | wherein the second set of allele-specific oligonucleotide primers and the second common primer are useful in detecting in biological fluid the presence of a mutated K-ras gene sequence in the twelfth codon at position 2.

24. The diagnostic kit of claim 22 wherein the peptide nucleic acid is complementary to a segment of a sense strand of the DNA.

* * * * *